US006695786B2

United States Patent
Wang et al.

(10) Patent No.: US 6,695,786 B2
(45) Date of Patent: Feb. 24, 2004

(54) GUIDE AND POSITION MONITOR FOR INVASIVE MEDICAL INSTRUMENT

(75) Inventors: Shih-Ping Wang, Los Altos, CA (US); Shengtz Lin, Cupertino, CA (US); Siqing Zhang, Sunnyvale, CA (US); Donald Chin, Palo Alto, CA (US); Karen D. Maroc, San Jose, CA (US)

(73) Assignee: U-Systems, Inc., San Jose, CA (US)

( * ) Notice: Subject to any disclaimer, the term of this patent is extended or adjusted under 35 U.S.C. 154(b) by 0 days.

(21) Appl. No.: 10/100,649

(22) Filed: Mar. 18, 2002

(65) Prior Publication Data

US 2002/0156376 A1 Oct. 24, 2002

Related U.S. Application Data

(60) Provisional application No. 60/276,396, filed on Mar. 16, 2001, and provisional application No. 60/329,235, filed on Oct. 12, 2001.

(51) Int. Cl.[7] ............................................... A61B 8/14
(52) U.S. Cl. ..................... 600/461; 600/437; 600/464; 600/417
(58) Field of Search ................................. 600/407–472

(56) References Cited

U.S. PATENT DOCUMENTS

| | | | | |
|---|---|---|---|---|
| 4,058,001 A | * | 11/1977 | Waxman | 600/443 |
| 4,058,114 A | * | 11/1977 | Soldner | 600/461 |
| 4,346,717 A | | 8/1982 | Haerten | |
| 4,469,106 A | | 9/1984 | Harui | |
| 4,567,896 A | * | 2/1986 | Barnea et al. | 600/443 |
| 4,576,175 A | * | 3/1986 | Epstein | 600/461 |
| 4,582,061 A | | 4/1986 | Fry | |
| 4,681,103 A | | 7/1987 | Boner et al. | |
| 4,733,661 A | | 3/1988 | Palestrant | |
| 4,838,506 A | | 6/1989 | Cooper | |

(List continued on next page.)

OTHER PUBLICATIONS

"New for the Falcon 2101 Scanner—High Resolution Small Part Scanning," 1–page information sheet from: www.bk-med.com/application/Applications/General%20Ultrasound/smallparts.htm, printed Sep. 11, 2000.

Ultramark 9 HDI Reference Manual 4703–0013–05, p. 32–5, Advanced Technology Laboratories, Bothell, Washington.

"Break–through in Interventional Ultrasound: UltraGuide 1000: Electronic Guidance for Free–hand Procedures," 6–page product literature guide from UltraGuide, Inc., Lakewood, Colorado (undated).

"UltraGuide 1000 System," 4–page product literature guide from UltraGuide, Inc., Lakewood, Colorado (1998).

*Primary Examiner*—Dennis Ruhl
*Assistant Examiner*—William C. Jung
(74) *Attorney, Agent, or Firm*—Cooper & Dunham LLP

(57) ABSTRACT

An instrument guide is described for mounting an invasive instrument such as a biopsy needle to an imaging probe, controlling its position, monitoring its position, and/or predictively displaying its position on a user display of the medical imaging system. A plurality of substantially rigid segments are hingeably connected to the probe, to an instrument handle, and to each other such that movement of the biopsy needle is restricted to within the imaged plane. However, substantial freedom of movement within the imaged plane is provided such that the instrument may be inserted into the patient over a wide range of angles. In one preferred embodiment, angle detectors are provided at each segment intersection and measurements provided for computing and displaying the instrument position and orientation on the user display. The instrument guide/position monitor is preferably made with low-cost components such that it is disposable after a single use. A predictive user display is provided in which the throw of a spring-loaded instrument is shown on the user display, the throw corresponding to the space that the instrument will occupy after a spring trigger is activated.

48 Claims, 12 Drawing Sheets

U.S. PATENT DOCUMENTS

| | | | |
|---|---|---|---|
| 4,898,178 A | | 2/1990 | Wedel |
| 4,899,756 A | * | 2/1990 | Sonek ........................ 600/461 |
| 5,052,396 A | | 10/1991 | Wedel et al. |
| 5,076,279 A | | 12/1991 | Arenson et al. |
| 5,095,910 A | * | 3/1992 | Powers ....................... 600/461 |
| 5,170,790 A | | 12/1992 | Lacoste et al. |
| 5,235,987 A | | 8/1993 | Wolfe |
| 5,494,039 A | | 2/1996 | Onik et al. |
| 5,572,999 A | | 11/1996 | Funda et al. |
| 5,623,931 A | | 4/1997 | Wung et al. |
| 5,647,373 A | * | 7/1997 | Paltieli ....................... 600/567 |
| 5,660,185 A | * | 8/1997 | Shmulewitz et al. ....... 600/562 |
| 5,758,650 A | | 6/1998 | Miller et al. |
| 5,810,008 A | | 9/1998 | Dekel et al. |
| 5,873,828 A | | 2/1999 | Fujio et al. |
| 5,920,395 A | | 7/1999 | Schulz |
| 5,924,992 A | * | 7/1999 | Park et al. ................... 600/461 |
| 5,941,889 A | | 8/1999 | Cermak |
| 5,984,930 A | | 11/1999 | Maciunas et al. |
| 6,171,249 B1 | | 1/2001 | Chin et al. |
| 6,216,029 B1 | * | 4/2001 | Paltieli ....................... 600/427 |

* cited by examiner

GUIDE AND POSITION MONITOR FOR INVASIVE MEDICAL INSTRUMENT

CROSS-REFERENCE TO RELATED APPLICATIONS

This application claims the benefit of prior U.S. Provisional Application No. 60/276,396, filed Mar. 16, 2001, which is incorporated by reference herein. This application also claims the benefit of prior U.S. Provisional Application No. 60/329,235, filed Oct. 12, 2001, which is incorporated by reference herein.

FIELD

This patent specification relates to medical procedures such as ultrasound-assisted biopsies in which an invasive medical instrument such as a biopsy needle is guided by a medical imaging system such as an ultrasound system. More particularly, it relates to a low-cost apparatus for mounting the instrument to an imaging probe, controlling its position, monitoring its position, and/or predictively displaying its position on a user display of the medical imaging system.

BACKGROUND

Ultrasound imaging systems have become increasingly popular for use in medical applications because they are non-invasive, easy to use, capable of real-time operation, and do not subject patients to the dangers of electromagnetic radiation. Instead of electromagnetic radiation, an ultrasound imaging system transmits sound waves of very high frequency (e.g., 1 MHz to 15 MHz) into the patient and processes echoes from structures in the patient's body to derive and display information relating to these structures. Although the preferred embodiments are described infra with respect to an ultrasound imaging environment, it is to be appreciated that they are also applicable in the context of other medical imaging environments including computerized tomography (CT), magnetic resonance imaging (MRI), and other environments.

Among other useful applications, ultrasound imaging systems are used in invasive surgical procedures such as biopsies. In such a use, the ultrasound imaging system is used to locate a region of interest in the patient, such as a tumor, and to assist the doctor or other medical professional (hereinafter "user") in guiding a biopsy needle to the tumor. As known in the art, ultrasound imaging systems generally only provide an image of a single plane within the patient as determined by the position and orientation of the ultrasound probe head. In particular, the imaged plane is usually a plane defined by the intersection of two lines, the first line being along a transducer array surface of the probe head, the second line being perpendicular to the first line along a center axis of the probe head. It is necessary to keep the biopsy needle positioned within the imaged plane in order for it to remain visible on the ultrasound monitor during the procedure.

Biopsy needle guides have been proposed for attaching biopsy needles to ultrasound probes and restricting movement of biopsy needles to the imaged plane. FIG. 1 illustrates a needle guide 100 proposed in U.S. Pat. No. 5,623,931, which is incorporated by reference herein, in which a probe clip 110 attaches to an ultrasound probe, and in which the biopsy needle is slidably guided by one of three grooves 111, thereby constraining its movement to within the imaged plane. FIG. 2 illustrates a needle guide 19 proposed in U.S. Pat. No. 4,899,756, which is incorporated by reference herein, in which the needle is rotatably affixed to a two-link structure that is, in turn, rotatably affixed to the ultrasound probe. The two-link structure comprises an "ascending link" 22 affixed to the ultrasound probe that is rotatable only in the imaged plane, and a "descending link" 23 that is slidably affixed to the ascending link and rotatable only in the imaged plane. The biopsy needle is thereby constrained to the imaged plane.

The medical realities of many biopsy procedures, including breast tumor biopsy procedures, render the needle guides of FIG. 1 and FIG. 2 insufficient for many practical situations. Many breast tumor biopsy procedures require a substantial number of different samples or insertions into the tumor, often at incrementally different positions and/or angles. It is often desirable to allow the user to maintain the probe head in a fixed position, thereby keeping the tumor position constant on the ultrasound output screen, while gently and incrementally adjusting the positioning and angle of the needle. As another example, because it is crucial not to puncture the chest wall and lung during the procedure, it is often desirable to insert the needle into the patient at an angle that is approximately parallel to the transducer surface, i.e. at an angle that is approximately 90 degrees from the probe axis. In this way, the ultrasound probe may be placed at a stable position perpendicular to the chest wall on top of the breast, while the needle is inserted at an angle parallel to the chest wall, thereby reducing the possibility of chest wall and lung puncture. Even further, it is desirable to have the ability to place the transducer surface on one side of the breast, while allowing the biopsy needle to be inserted on the other side of the breast, whereby the biopsy needle may enter the breast at an angle up to 180 degrees with respect to the probe axis. Still further, it is often desirable to insert the needle at a direct zero-degree angle with respect to the probe axis at a point directly adjacent to the transducer array.

While the needle guide of FIG. 2 allows more freedom of needle movement than the device of FIG. 1, it nevertheless presents substantial restrictions on needle movement and position within the imaged plane. For example, the two-link device is not readily amenable to allowing the zero-degree insertion (i.e., parallel to probe axis) of a biopsy needle at a point adjacent to the probe head, or of allowing a 180-degree insertion at a breast point opposite the probe head. It would be desirable to provide a biopsy needle guide that allows for substantially unfettered freedom of movement of a biopsy needle within the imaged plane of an ultrasound system, both in terms of needle angle and needle entry point.

Moreover, because a biopsy needle represents a thin, and often specular, target for the ultrasound system, it is often difficult for the ultrasound system to maintain a clear output image of the biopsy needle that is easily viewable. A clear image of the biopsy needle can be difficult to obtain even if its movement is restricted to the imaged plane. One method for dealing with this problem involves the performance of image recognition algorithms on the ultrasound image to identify and segment the biopsy needle, with the needle position and orientation then being highlighted on the display screen. The needle highlight usually comprises a bright-colored or otherwise noticeable line positioned at the computed needle position. Unfortunately, the image recognition algorithms often require extensive processing power, and output frame rates can suffer accordingly. Also, these image processing algorithms can at least partially fail if the needle wanders from the imaged plane. Finally, because of the appreciable amount of computation required, quick movements of the biopsy needle can cause jittery and/or delayed needle highlights.

Another method for dealing with needle visualization problems during ultrasound-assisted biopsy procedures is to mount three-dimensional position and orientation sensors, such as magnetic sensors, on the ultrasound transducer and the biopsy needle handle. The position and orientation sensors provide the position (x,y,z) and orientation (ρ,θ,φ) of both the transducer and the needle handle to the ultrasound system. This allows for prompt computation of the position and orientation of the biopsy needle relative to the ultrasound image slice being displayed. The biopsy needle is manipulated "free-hand" and can depart from the imaged plane, with special designations on the highlighted display to indicate departure from the imaged plane. An example of one such system is the UltraGuide® 1000 available from UltraGuide, Inc. of Lakewood, Colo.; see also U.S. Pat. No. 6,216,029, which is incorporated by reference herein.

One or more practical disadvantages, however, are associated with systems based on three-dimensional position and orientation sensing. First, although they allow for "free-hand" operation of the biopsy needle, the three-dimensional sensing hardware is quite expensive, whether it be based on magnetic sensing systems, accelerometers, or gyro-based systems. Second, in several medical procedures including breast biopsies, it has been found that "free-hand" operation of the biopsy needle is often less desirable, with users preferring to be assisted by a mechanical needle support/constraint. Third, for many users the experience can be awkward and overly complicated, as they are required to simultaneously (i) manipulate the ultrasound transducer with one hand, (ii) manipulate the unsupported, unconstrained biopsy needle with the other hand, and (iii) observe and interpret needle highlights that are not always intuitive to understand. This is especially problematic because the unconstrained "free-hand" needle will often depart from the imaged plane, requiring the user to interpret special markings on the two-dimensional ultrasound display in trying to visualize the three-dimensional events. One attempt to remedy this problem is found in the UltraGuide® 1000 system, in which an animated three-dimensional perspective view of the needle and the imaged plane is placed beside the two-dimensional ultrasound slice. However, this requires the user to observe and interpret yet another computer output simultaneously with all of the other actions and observations then occurring. This can be an excessive requirement even for sophisticated users. Moreover, this also entails an additional layer of computational complexity for the ultrasound system. Fourth, because of the expensive nature of the three-dimensional sensing equipment involved, this equipment needs to be reused over many patients. This can increase the risk of contagious disease transmission unless careful sterilization and/or prophylactic measures are taken after each and every patient.

Accordingly, it would be desirable to provide a probe-mounted instrument guide for facilitating medical procedures in which an invasive medical instrument is guided by a medical imaging system, the probe-mounted instrument guide the allowing for substantially unfettered freedom of movement of the instrument within an imaged plane of a medical imaging system, both in terms of instrument angle and instrument entry point.

It would be further desirable to provide a probe-mounted instrument guide and position monitor for facilitating such medical procedures, the guiding and monitoring apparatus being easy and intuitive to use.

It would be even further desirable to provide such a guiding and monitoring apparatus that is low in cost to produce, such that it can be disposed of after a single use, thereby reducing risk of contagious disease transmission among successive patients.

SUMMARY

According to a preferred embodiment, a probe-mounted instrument guide is provided comprising a plurality of rigid links or segments, including a first segment connected to the probe, a final segment connected to a handle of the instrument, and one or more intermediate segments coupled therebetween. The segments are hingeably coupled such that movement of the biopsy needle is restricted to the imaged plane. Preferably, there are at least three segments for allowing sufficient movement of the biopsy needle in the imaged plane, e.g., for allowing needle entry into the patient at a wide range of entry points and entry angles as required during many breast biopsies. The segments preferably comprise a low-cost but substantially rigid and easy-to-manipulate plastic material.

Advantageously, a needle-guiding apparatus in accordance with the preferred embodiments can be produced at very low cost, and therefore can be a disposable device. This is important in today's clinical settings, in which medical imaging hardware can act as fomites for transmitting contagious diseases from patient to patient unless proper sterilization and/or prophylactic measures are taken. Here, the needle-guiding apparatus can simply be discarded along with the disposable needle and needle handle after the biopsy procedure.

According to another preferred embodiment, a low-cost apparatus is provided for also monitoring the position of a medical instrument while restricting its movement to the desired imaged plane. In another preferred embodiment, predictive monitoring of the position of the medical instrument is provided on a user display. According to a preferred embodiment, angle detectors are provided at each segment intersection. Information from the angle detectors is provided to the medical imaging system, which then readily calculates the position and orientation of the needle and superimposes a needle position indicator or highlighter on the user display.

Advantageously, in contrast to the sophisticated sensors required in three-dimensional free-space position detection systems, the angle detectors at the segment intersections can be procured at very low cost. Therefore, the needle guiding and position-detection apparatus can still be a disposable device. By way of example, the angle detectors may comprise low-cost position encoders such as optical position encoders or electrical potentiometers. Other angle detector types, such as those based upon angle-dependent inductive coupling or angle-dependent capacitive coupling, can be used. Optionally, for even further cost savings, the position encoders themselves can serve the mechanical coupling means between segments.

According to another preferred embodiment, the medical imaging system is configured to highlight the biopsy needle in a predictive manner, i.e., to display a projection of the needle based on its current position and orientation. Accordingly, even if the biopsy needle is outside the field of view of the imaged plane being displayed, its projection will appear on the display. This can be of great assistance in guiding the biopsy needle to the desired target location. If the biopsy needle is spring-loaded or is otherwise slidably coupled to its handle, an additional sensor on the needle handle provides the ultrasound system with this required data point.

The angle information corresponding to the respective link intersections may be transmitted to the medical imaging system in any of a variety of ways. In one preferred embodiment, which is likely to be the lowest-cost embodiment, electrical wires are connected to each angle encoder and run down the assembly to a common, standardized connector for connection to the medical imaging system. When there are several encoders, a common ribbon cable can be used to simplify the appearance and manipulation of the assembly. In other preferred embodiments, fiber optic cables can be used. In still other preferred embodiments, small RF transmitters, infrared transmitters, or optical transmitters may be used to communicate the angle information to the medical imaging system. A needle-guiding and position detecting apparatus in accordance with the preferred embodiments is readily applicable in ultrasound environments, computerized tomography (CT) environments, magnetic resonance imaging (MRI) environments, and other medical imaging environments.

DESCRIPTION

Figure 3:
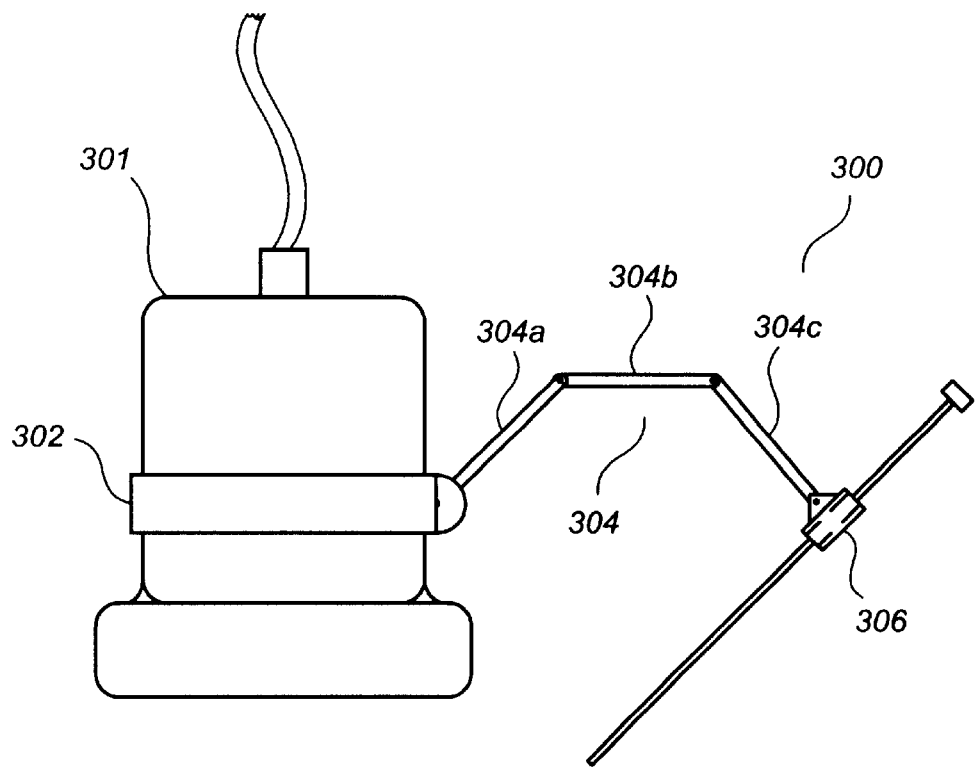
FIG. 3 illustrates a side view of a medical instrument guide according to a preferred embodiment.

FIG. 3 illustrates a medical instrument guide in accordance with a preferred embodiment coupled to an imaging probe, in particular, a biopsy needle guide 300 coupled to an ultrasound probe 301. Needle guide 300 comprises a brace 302, a link assembly 304, and a needle holder 306 as shown in FIG. 3. According to a preferred embodiment, link assembly 304 comprises at least three links elements, denoted 304a, 304b, and 304c in FIG. 3, for providing greater freedom of movement in the imaged plane. Brace 302, link assembly 304, and needle holder 306 may comprise metal or plastic materials of sufficient rigidity, and are preferably selected such that the needle guide 300 is low cost for disposability, and/or such that portions thereof (e.g., just the link assembly 304 and needle holder 306) are low cost for disposability. The link elements are rotatably affixed to each other as shown, such that rotation occurs within the imaged plane but such that it is difficult or impossible to twist or bend the biopsy needle to a position outside the imaged plane. The needle holder 306 is designed to hold any standard biopsy needle.

Figure 1:
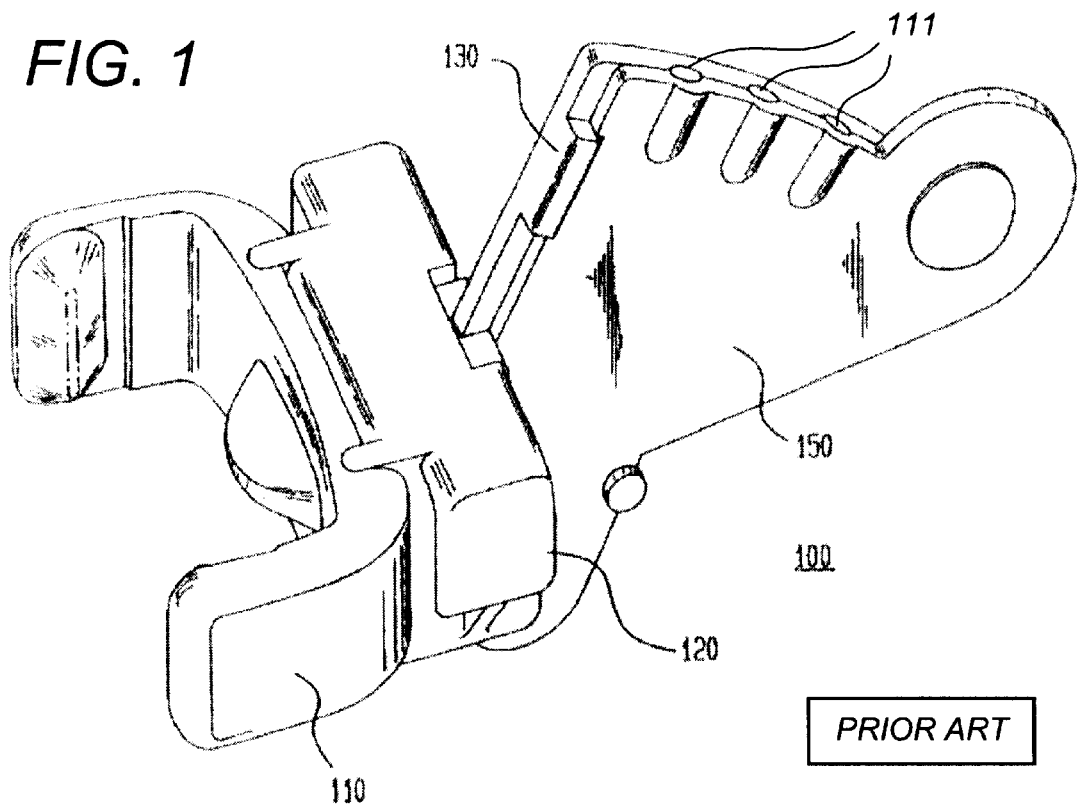
FIG. 1 illustrates a prior art probe-mounted needle guide.
Figure 2:
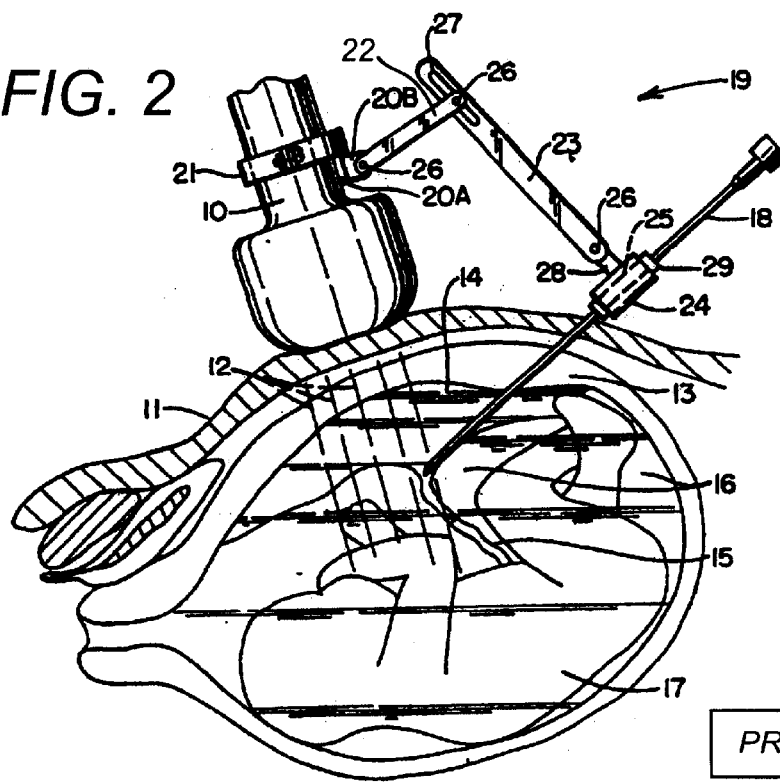
FIG. 2 illustrates a prior art probe-mounted needle guide.
Figure 4:
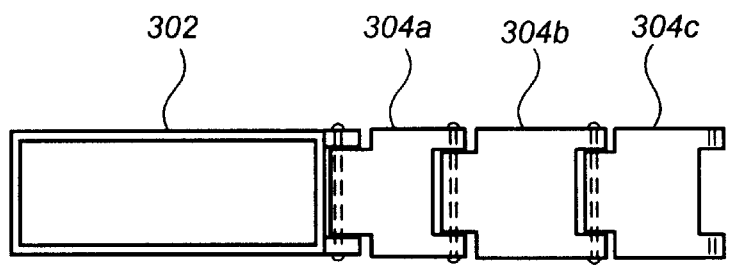
FIG. 4 illustrates a top view of the medical instrument guide of FIG. 3.

Any of a variety of materials, joint types, and joint configurations may be selected for the brace 302, link assembly 304, and needle holder 306. While brace 302 is shown in FIG. 3 as a banded structure placed around the probe head, the brace 302 may be of any type sufficient to rigidly attach the needle guide assembly 300 to the probe 301, one example being the open clamped-type element 110 of FIG. 1, another example being the element 21 of FIG. 2. Although not shown in FIG. 3, the brace 302 preferably comprises means for tightening its clamping strength around the probe head, for example a screw-type tightening element similar to element 21 of FIG. 2. With reference to FIG. 4, which shows a detached top view of the brace 302 and link assembly 304, it has been found that hard plastic planar link elements oriented perpendicular to the imaged plane, coupled by joint elements such as hard plastic joint rods that are also positioned perpendicular to the imaged plane, are particularly useful for forming the link assembly 304. The hinges shown in FIG. 4 are one type of pin-in-slot hinge, which refers generally to a wide variety of hinges that use a central pin, rod, nut, or the like around which the link assembly members rotate. However, the scope of the preferred embodiments is not so limited and any of a variety of materials and joint configurations may be selected for the link assembly 304. As the number of link elements is increased, the angular and positional freedom of the biopsy needle is increased. However, it is also necessary to incorporate elements that are more rigid and stable as the number of link elements is increased so that the biopsy needle continues to be effectively restricted to the imaged plane.

Figure 5A:
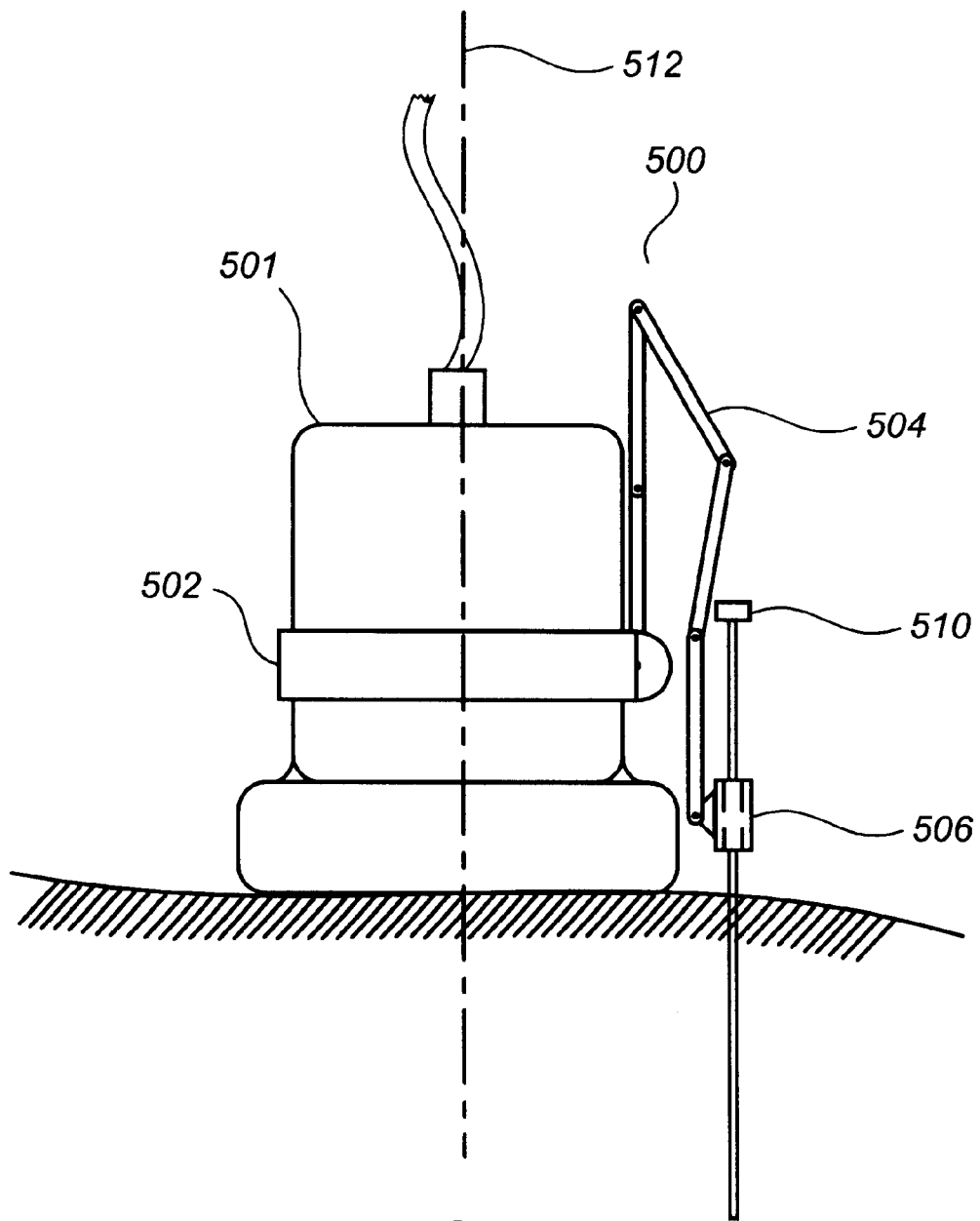
FIGS. 5A–5C illustrate side views of a medical instrument guide according to a preferred embodiment.
Figure 5B:
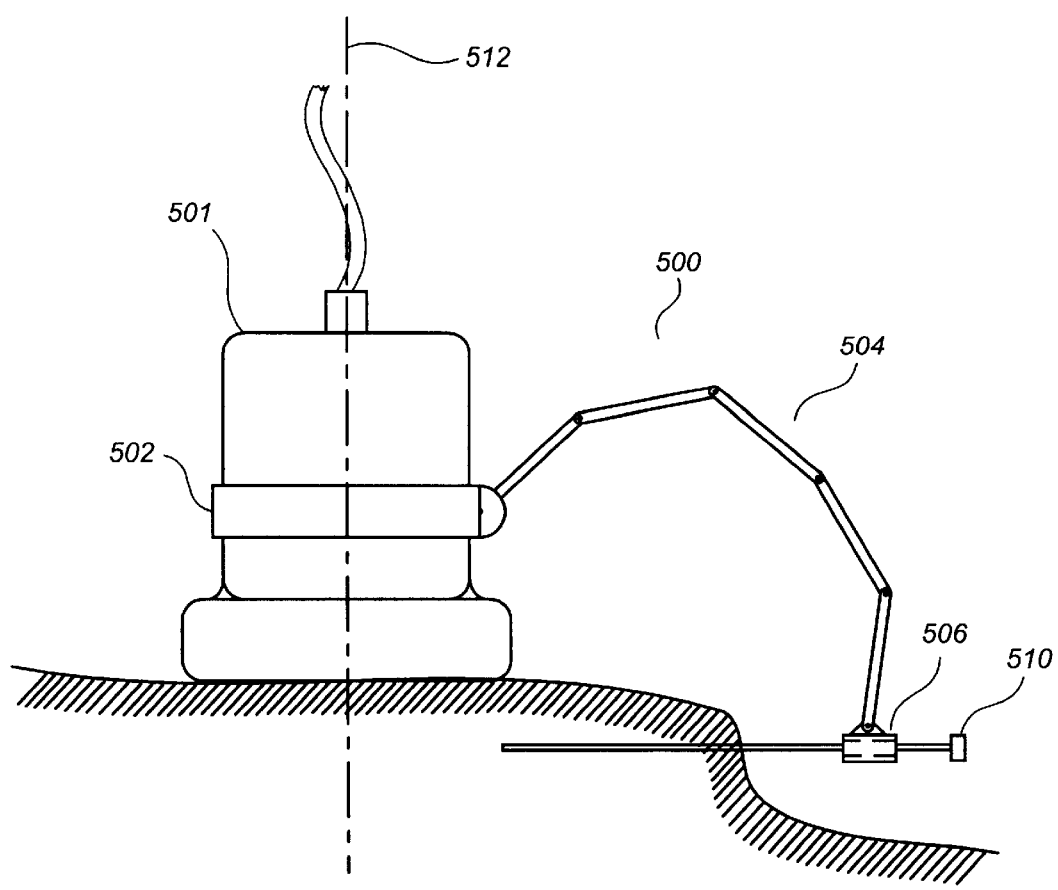
Figure 5C:
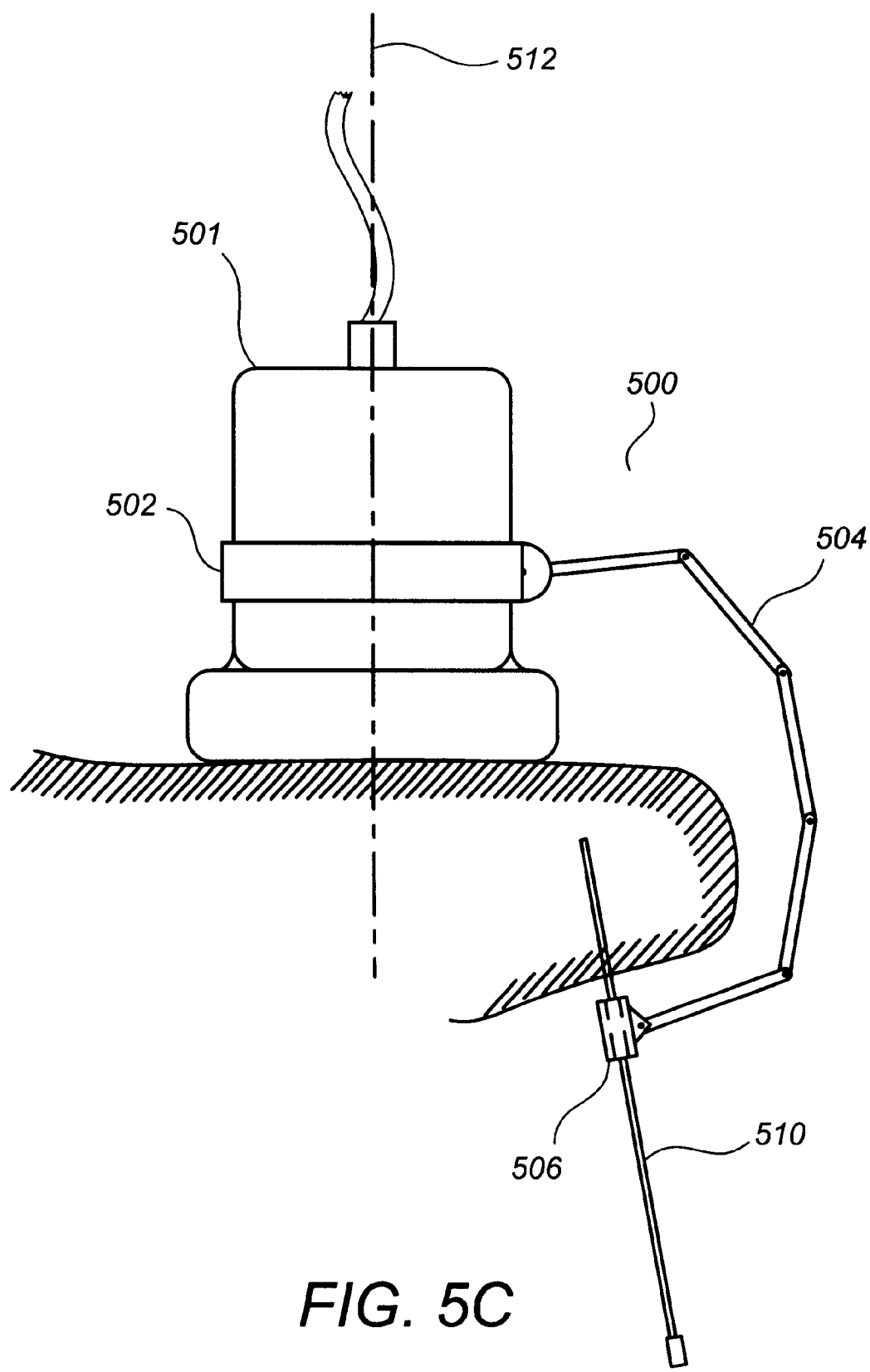

FIGS. 5A, 5B, and 5C show a biopsy needle guide 500 in accordance with a preferred embodiment comprising a brace 502, a link assembly 504, and a needle holder 506, wherein the link assembly 504 comprises five link elements. FIG. 5A shows a simplified diagram of the needle guide 500 guiding a needle 510 into the patient at a zero degree angle with respect to a probe axis 512 at a point adjacent to the probe head 501. FIG. 5B illustrates the needle 510 being guided at a 90 degree angle with respect to the probe axis 512 at a point distant from the probe head, while FIG. 5C illustrates the needle 510 being guided into the patient's breast on the other side of the breast, at an angle that is almost 180 degrees with respect to the probe head. As evidenced in FIGS. 5A–5C, the preferred embodiments provide the user with full freedom within the imaged plane to access the tumor at any angle from any point of entry with respect to the ultrasound probe head. Advantageously, substantial positional and angular freedom of movement is allowed while at the same time the needle is restricted to the imaged plane.

Figure 6:
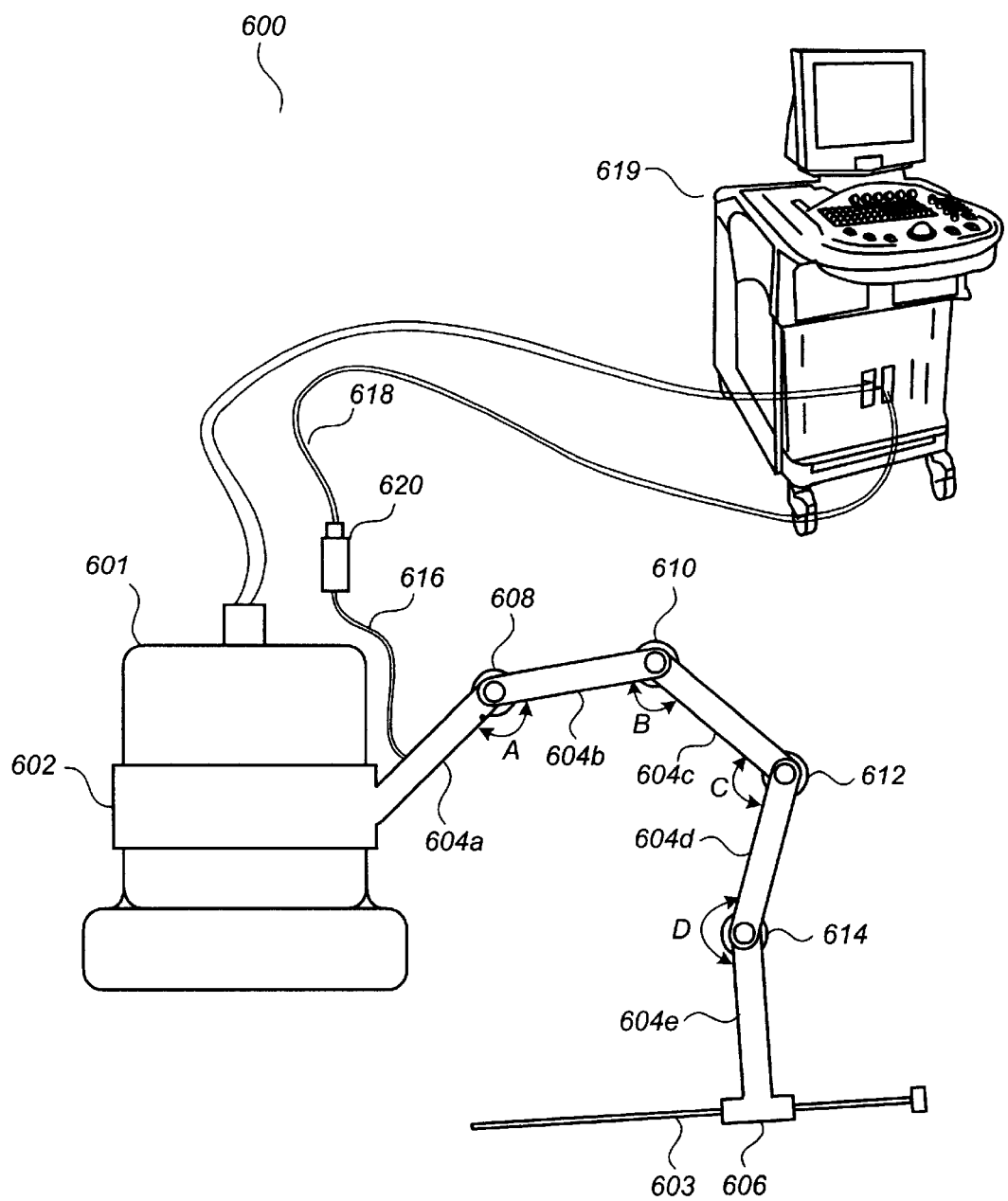
FIG. 6 illustrates a side view of a medical instrument guide with position detection capability according to a preferred embodiment.

FIG. 6 illustrates a biopsy needle guide and position monitor 600 (hereinafter "guide/monitor 600") in accordance with a preferred embodiment, as coupled to an ultrasound probe 601 and an associated ultrasound system 619. Guide/monitor 600 comprises a brace 602, a plurality of rigid links or arm segments 604a–604e, a needle holder 606, and a plurality of angle detectors or encoders 608–614 positioned as shown in FIG. 6. For simplicity and clarity of disclosure, it is assumed that the first segment 604a is integral with the brace 602 and that the last segment 104e is integral with the needle holder 606. However, in general the first and last segments may also be hingeably coupled to their anchor points, with encoders provided at these points to measure the intersection angle. Additionally, the needle holder 606 may be provided with a lateral position encoder (not shown) in the event that the needle 603 is slidably attached thereto. In the event that there is a spring-triggered needle holder in which the needle 603 is kept in one of only two positions, a very simple switch device can be used.

Encoders 608–614 may comprise any of a variety of well-known position encoders such as optical encoders or potentiometers. Other angle detector types, such as those based upon angle-dependent inductive coupling or angle-dependent capacitive coupling, can be used. For electrical encoders such as potentiometers, signals are sent to the ultrasound system 619 over a signal wire 616, which is coupled to a dedicated signal wire 618 leading to the ultrasound system 619 by a detachable connector 620. The ultrasound system 619 includes equipment for receiving the angle information and a processor configured to process that information as described herein. The signal wire 616 is coupled to each of the encoders 608–614, these connections being hidden from view in FIG. 6. The position and orientation of the biopsy needle 603 is readily computed from knowledge of the intersection angles A, B, C, and D and knowledge of the length of each of the segments 604a–604e. In other embodiments, small RF transmitters, infrared transmitters, or other optical, acoustic, or electromagnetic transmitters may be used to communicate the angle information to the ultrasound system. Advantageously, the amount of data being transmitted is very small, and so inexpensive, low-bandwidth wireless devices (e.g., infrared transmitters similar to those used in television remote controls) can be used.

According to a preferred embodiment, the link assembly between the ultrasound probe 601 and the needle holder 606 comprises at least three links elements for providing greater freedom of movement in the imaged plane. Brace 602, rigid segments 604, and needle holder 606 may comprise metal or plastic materials of sufficient rigidity, and are preferably selected such that cost of the guide/monitor 600 is kept low consistent with being a disposable, single-use device. On one preferred embodiment, the material used comprises PET (polyethylene terephthalate) plastic. The segments are rotatably affixed to each other as shown, such that rotation occurs within the imaged plane but such that it is difficult or impossible to twist or bend the biopsy needle 603 to a position outside the imaged plane. The needle holder 606 is designed to hold any standard biopsy needle. Any of a variety of materials, joint types, and joint configurations may be selected for the brace 602, link assembly 604a–604e, and needle holder 606.

Figure 7:
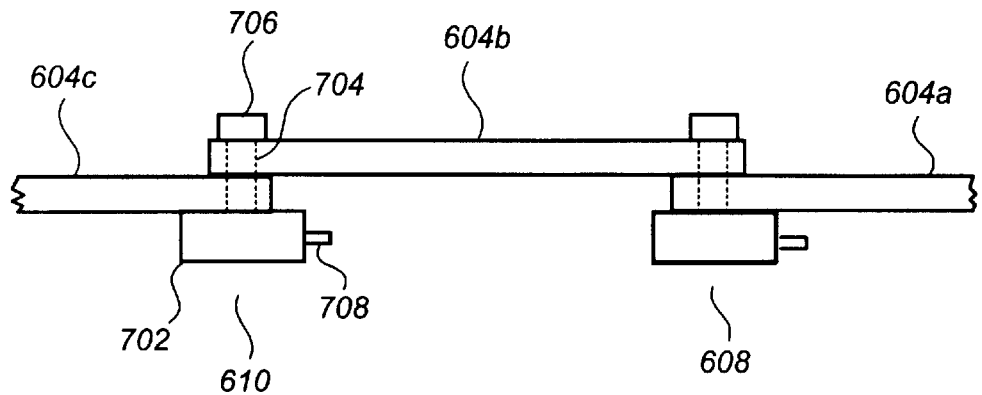
FIG. 7 illustrates a top view of the medical instrument guide of FIG. 6.
Figure 8:
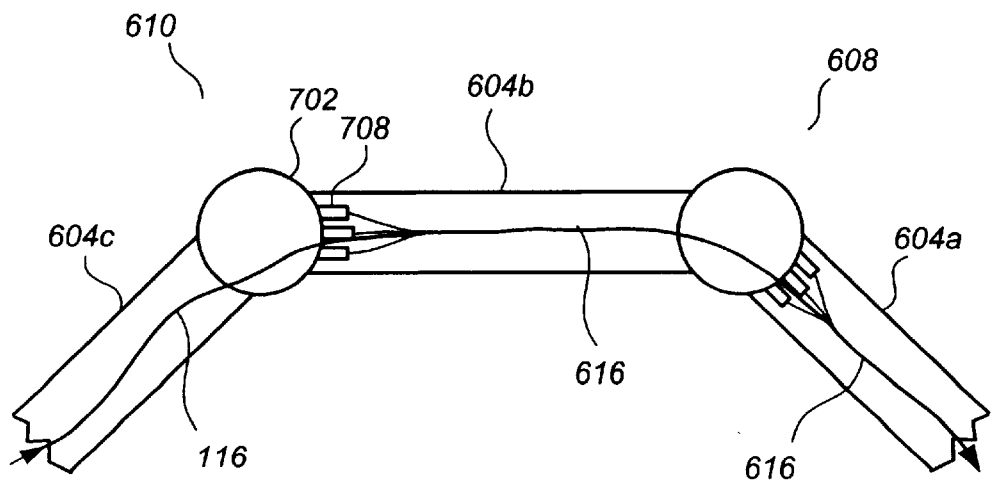
FIG. 8 illustrates reverse side view of the medical instrument guide of FIG. 6.

FIG. 7 illustrates a top view of a portion of the guide/monitor 600 taken from a reverse direction with respect to FIG. 6. FIG. 8 illustrates a corresponding reverse side view of that portion. As indicated in FIGS. 7–8, segment 604b is hingeably coupled to segments 604a and 604c at intersections therewith. According to a preferred embodiment, the hingeable coupling is achieved using the encoder assemblies themselves to provide the axis of rotation between segments, thereby further reducing system costs. In the embodiment shown in FIGS. 7–8, the encoder 610 comprises a simple, off-the-shelf electrical potentiometer having a housing 702, a shaft 704, and a knob 706. The housing 702 is fixably attached to the segment 604c, while the knob 706 is fixably attached to the segment 604b. As such, in addition to providing encoding functions, the encoder 610 also serves as the mechanical coupling between the successive arm segments, thereby reducing cost and complexity. Also shown in FIG. 8 for each of the encoders 608 and 610 are electrical contacts 708, which are coupled along signal wire 616 to the ultrasound system.

Figure 9A:
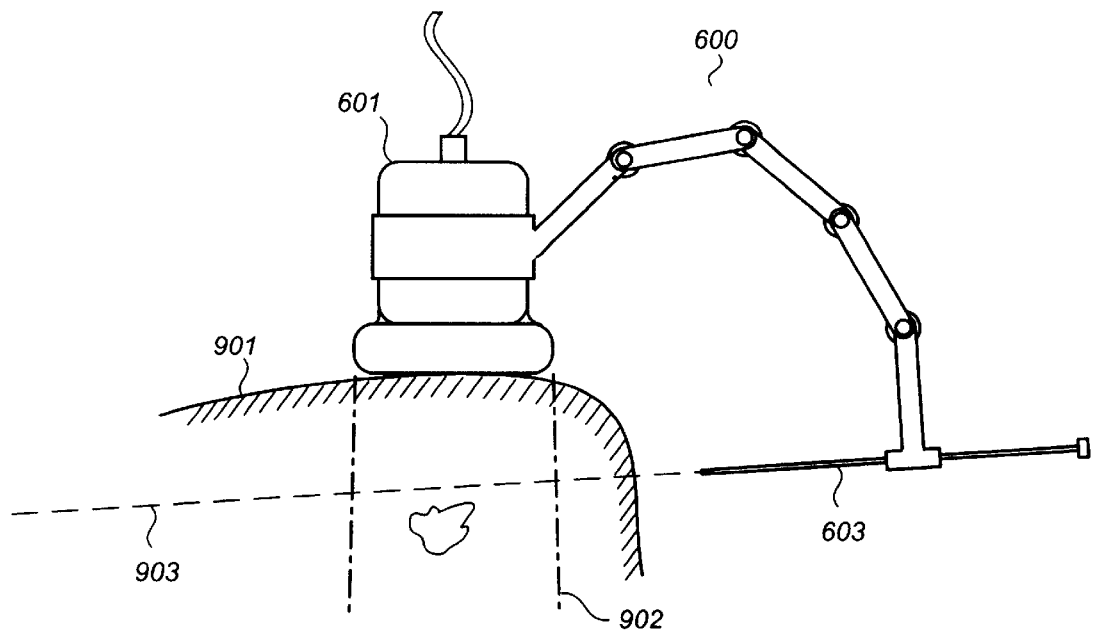
FIGS. 9A and 9B illustrate predictive medical instrument highlighting according to a preferred embodiment.
Figure 9B:
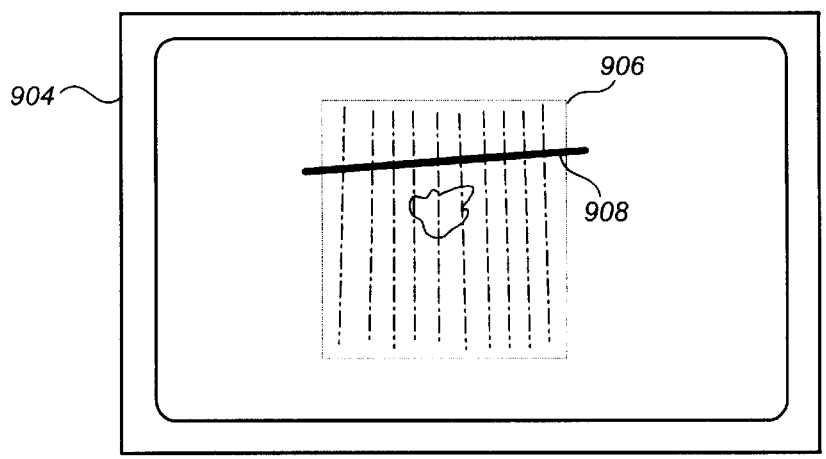

FIGS. 9A and 9B illustrate predictive biopsy needle highlighting according to a preferred embodiment. FIG. 9A illustrates the guide/monitor 600, ultrasound probe 601, and biopsy needle 603 positioned with respect to a target 901 such that the needle 603 is not inserted into the target tissue and remains out-of-view with respect to a viewable area 902. In FIG. 9B, the viewable area 902 is shown as ultrasound image area 906 on an ultrasound display 904. As indicated in FIG. 9A, if the biopsy needle 603 were to follow the exact direction in which it is pointing at that instant, it would follow a projection line 903. Advantageously, even though the biopsy needle 603 is out of range of the viewable area 902, the position and orientation of this projection line 903 is readily available to the ultrasound systems at all times. According to a preferred embodiment, a needle projection image 908 is displayed on the ultrasound display 904 at all times, or upon activation of this feature by the user. The needle projection image 908 can be useful in many ways, such as providing a good indication of where to first insert the biopsy needle. Advantageously, because the biopsy needle is supported and constrained to the imaged plane, interpretation of the ultrasound display 904 is highly intuitive, and the user is not required to cognitively reconstruct a three-dimensional scenario of a biopsy needle entering and exiting the imaged plane.

Figure 10:
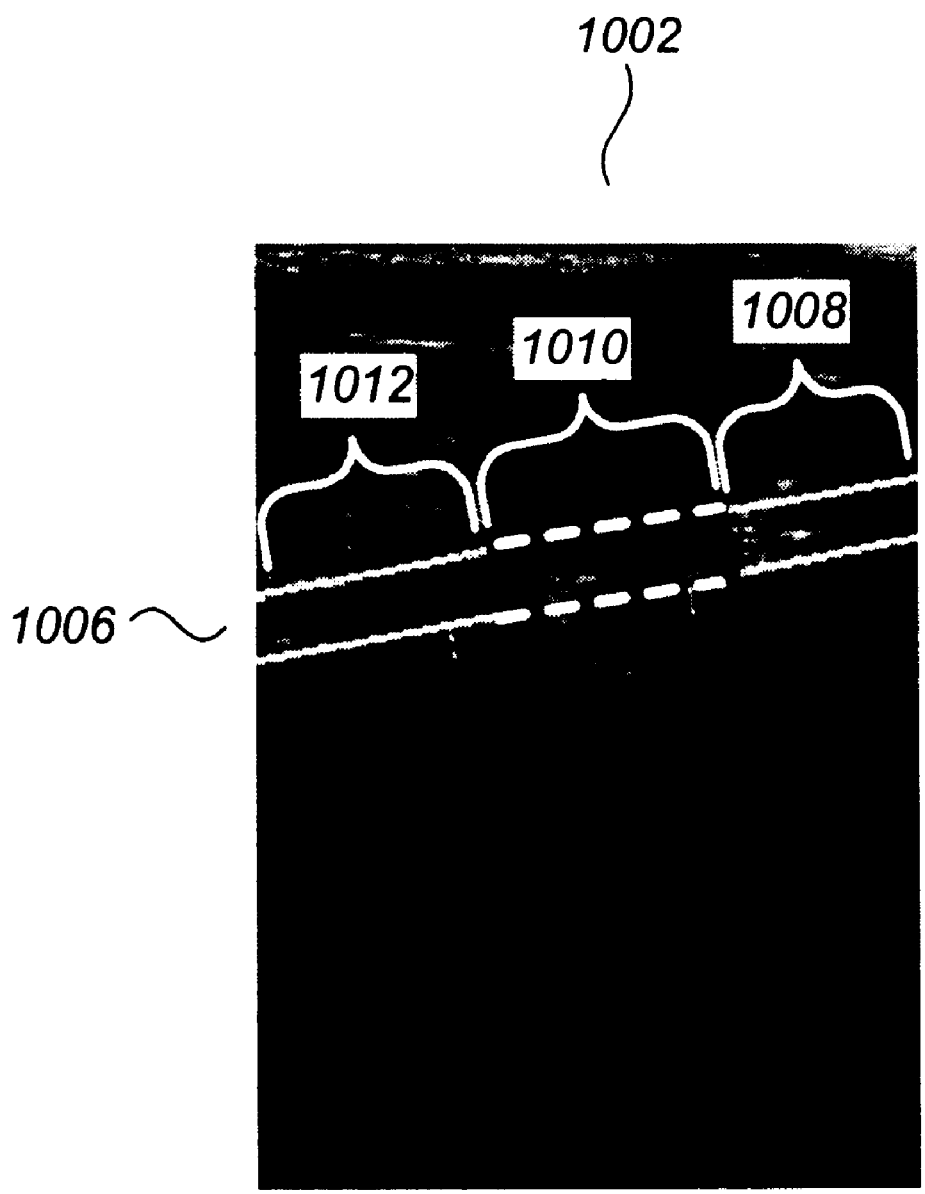
FIG. 10 illustrates a medical image output with instrument highlighting according to a preferred embodiment.

FIG. 10 illustrates an ultrasound image output 1002 with needle highlighting 1006 in accordance with a preferred embodiment. As with many actual images produced in clinical practice, the biopsy needle is difficult to see, appearing faintly between the lines on the right-hand side of FIG. 10. Needle highlighting 1006 comprises two lines on either side of the needle that are parallel with its direction. A first portion 1008 coincides with the actual needle penetration depth, while a second portion 1010 corresponds to a projected "throw" of a spring-loaded biopsy needle. That is, the region 1010 represents the future depth of the biopsy needle after the spring-loaded trigger is released. The portion 1012 is an extension that provides further assistance in locating and visualizing the biopsy needle.

Any of a variety of computer programs may be readily adapted by a person skilled in the art without undue experimentation to receive the encoded position information, compute the current needle position, provide the display outputs of FIGS. 9A–10, and to achieve other functionalities described herein based on the disclosure of this application. Examples include the software programs described in U.S. Pat. No. 6,325,759, and software associated with the VISTA™ Ultrasound Imaging System and Technology Platform available from U-Systems, Inc. of San Jose, Calif.

Figure 11:
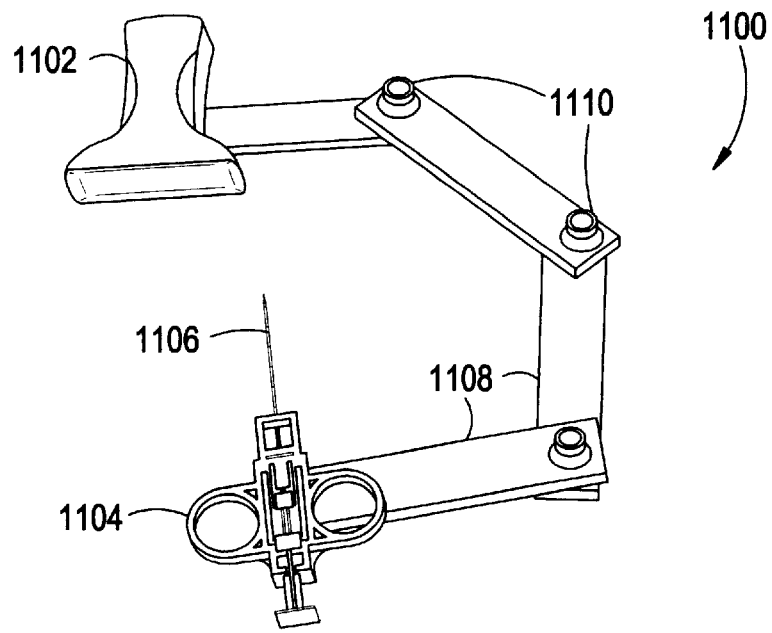
FIG. 11 illustrates a medical instrument guide according to a preferred embodiment.

FIG. 11 illustrates a medical instrument guide 1100 according to a preferred embodiment having a position detection capability, the medical instrument guide 1100 being attached at one end to an ultrasound probe 1102 and at the other end to a biopsy needle handle 1104 that holds a biopsy needle 1106. The biopsy needle handle 1104 has a spring-loaded mechanism for quickly penetrating into a lesion upon release of a trigger. The medical instrument guide 1100 comprises rigid segments 1108 made of PET plastic, and potentiometers 1110 that provide hingeable attachment of the segments to each other as well as position encoding capability. Wires (not shown) would be positioned behind the segments 1108 to connect the potentiometers 1110 to the medical imaging system over a connector (not shown).

Figure 12:
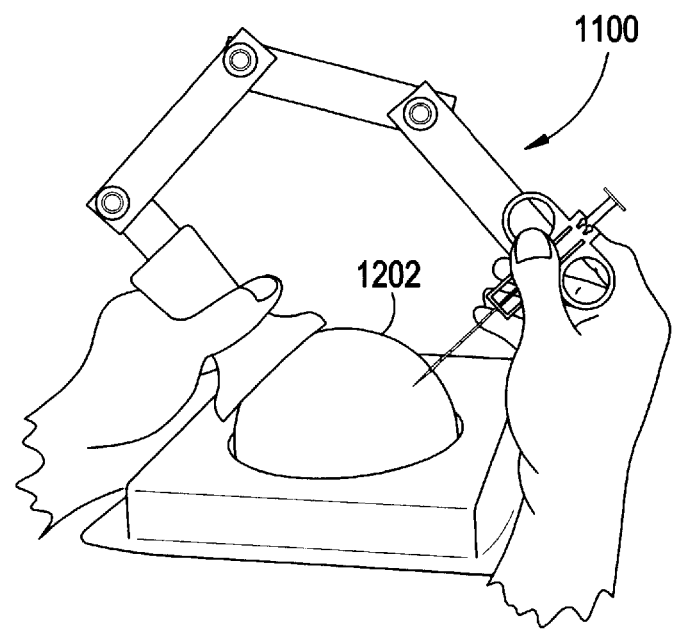
FIG. 12 illustrates a medical instrument guide according to a preferred embodiment.

FIG. 12 illustrates the medical instrument guide 1100 guiding a biopsy needle into a breast phantom 1202. In one preferred embodiment, the potentiometers 1110 may be Bourns type 6638 available from Bourns, Inc. of Riverside, Calif. The potentiometers may be coupled to the medical imaging system using a Dataq DI-700 12-bit multi-channel analog-to-digital converter, which interfaces to via a universal serial bus (USB) and is available from Dataq, Inc. of Akron, Ohio.

Figure 13:
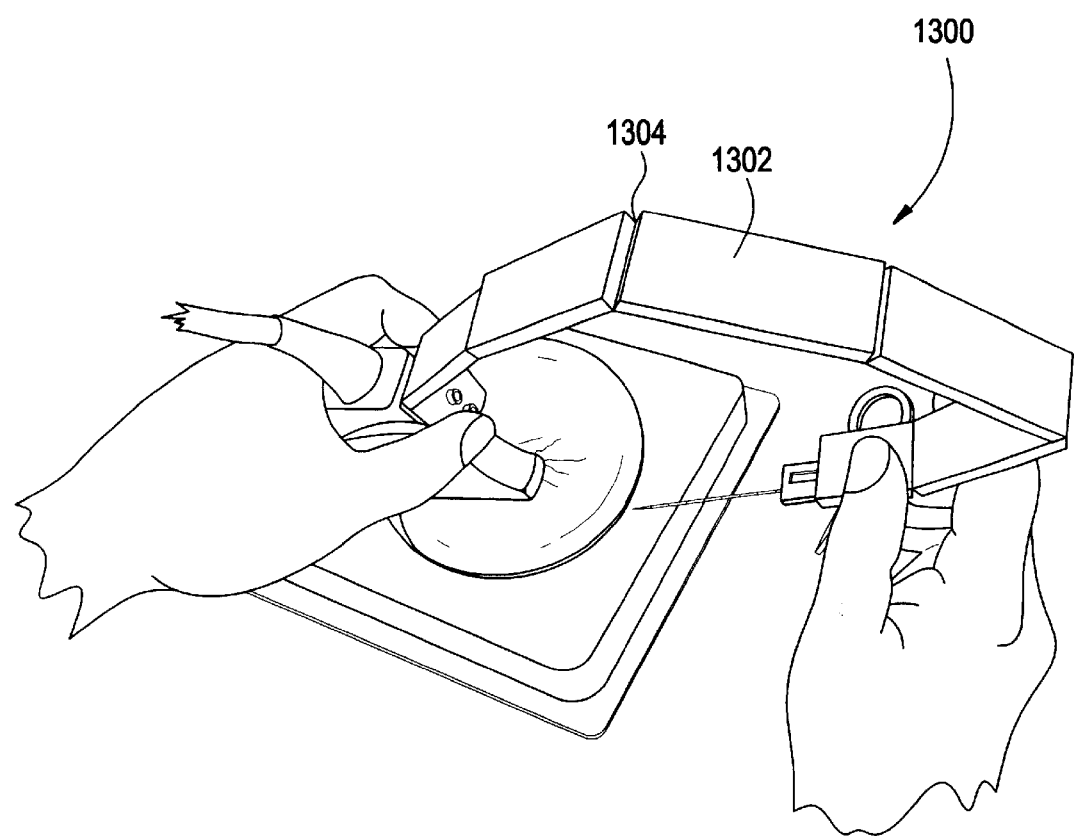
FIG. 13 illustrates a medical instrument guide according to a preferred embodiment.

FIG. 13 illustrates a medical instrument guide 1300 according to a preferred embodiment guiding a biopsy needle into a breast phantom. The medical instrument guide 1300 is similar to the guide 504 of FIGS. 5A–5C except that it comprises segments 1302 have rigid planar structures and that are positioned substantially perpendicular to the imaged plane. The segments 1302 are formed from a material such as a polypropylene plastic that provides substantial rigidity for each segment, but that at the same time allows integrated living hinge connections 1304 between the segments that simply comprise loci of reduced material thickness. To fabricate the device, a single sheet of polypropylene plastic, having a thickness for example of about 0.25 inches, has V-shaped grooves cut into it to form the living hinge connections. Such a device can be made at a substantially reduced cost as compared to the use of discrete mechanical hinge components, while at the same time providing good restriction of needle movement to the imaged plane.

Figure 14:
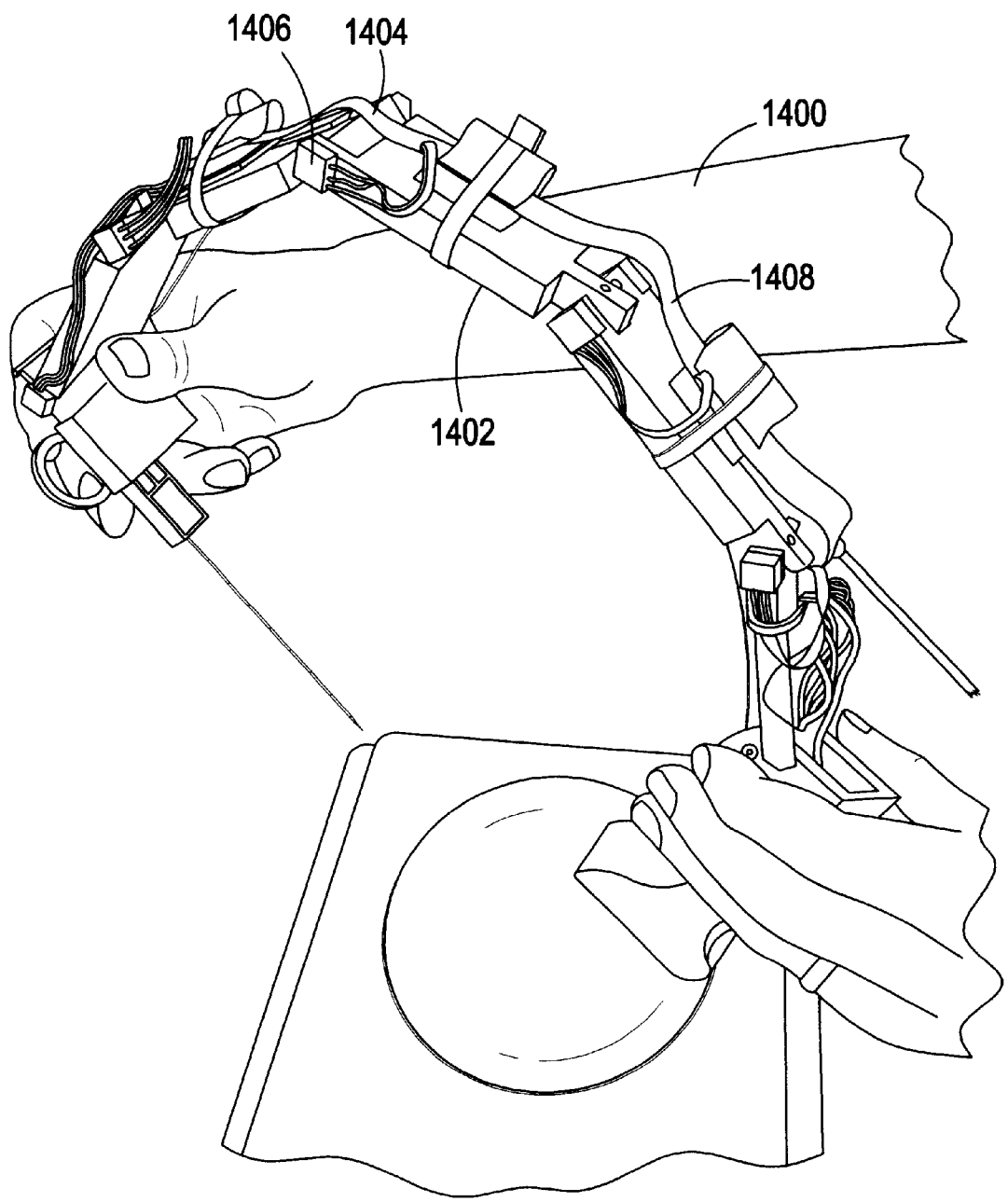
FIG. 14 illustrates a medical instrument guide according to a preferred embodiment.

FIG. 14 illustrates a medical instrument guide 1400 according to a preferred embodiment guiding a biopsy needle into a breast phantom. Medical instrument guide 1400 comprises segments 1402 comprising thick, planar slabs of plastic material oriented substantially perpendicular to the imaged plane. The thick planar slabs are hingeably connected by potentiometers 1404 that perform both hinge-coupling and position detecting functions. FIG. 14 shows potentiometer electrical connections 1406 and ribbon cables 1408 that provide electrical connectivity. It is to be appreciated, however, that the device of FIG. 14 is a prototype device, and that the somewhat ungainly appearance caused by the electrical connection components can be readily mitigated by using integrated and/or surface-mounted electrical connections known in the art in mass production. Segments 1402 can be solid or hollow.

Also provided in accordance with the preferred embodiments is a computer program product for the ultrasound system that receives the angle information, computes a current position of the biopsy needle relative to the ultrasound probe displays a representation of the biopsy needle on the user display for locations of overlap between the imaged plane and the biopsy needle according to FIGS. 9B–10. The computer program product further predictively projects the biopsy needle onto the user display based on the current position and orientation of the biopsy needle relative to the ultrasound probe according to FIGS. 9B–10.

According to another preferred embodiment, a biopsy needle or other medical instrument is mechanically guided in 3-dimensional space using, for example, link members that are coupled at ball joints. In this preferred embodiment, encoders at link member intersections measure angles corresponding to all three degrees of freedom at the ball joints, and the position and orientation of the biopsy needle can be computed from these measurements. Because the biopsy needle can depart the imaged plane, a somewhat more complex display system such as that discussed in the '029 patent, supra, would be required. Nevertheless, the advantages of low cost, disposability, and needle support are still provided.

Whereas many alterations and modifications of the preferred embodiments will no doubt become apparent to a person of ordinary skill in the art after having read the foregoing description, it is to be understood that the particular embodiments shown and described by way of illustration are in no way intended to be considered limiting. For example, while presented supra in the context of conventional ultrasound slices (as may be obtained in B-mode operation, for example), the preferred embodiments are readily applicable to ultrasound data acquired by any of a variety of ultrasound imaging modes such as color flow mode, power Doppler mode, or other two- or three-dimensional ultrasound imaging modes. Moreover, although described supra in terms of the control and monitoring of a biopsy needle during an ultrasound-assisted biopsy of a breast tumor, the preferred embodiments are advantageously used in a variety of invasive medical procedures in which a medical instrument is guided by a medical imaging system, and in which a low-cost apparatus is desired for mounting the instrument to an imaging probe, controlling its position, monitoring its position, and/or predictively displaying its position on a user display of the medical imaging system. Examples include CT-guided medical procedures and MRI-guided medical procedures. Therefore, reference to the details of the preferred embodiments are not intended to limit their scope, which is limited only by the scope of the claims set forth below.

What is claimed is:

1. An apparatus for coupling an invasive medical instrument to an imaging probe, the imaging probe having a substantially planar scanning field, comprising;
   a substantially rigid first link member that hingeably couples to the imaging probe such that relative movement of said first link member and the imaging probe is restricted around a first hinge axis substantially perpendicular to the scanning field plane;
   a substantially rigid second link member that hingeably couples to the medical instrument such that relative movement of said second link member and the medical instrument is restricted around a second hinge axis substantially perpendicular to the scanning field plane; and
   at least one substantially rigid intermediate link member hingeably coupled in a serial manner between said first and second link members, said apparatus substantially confining movement of the medical instrument to the scanning field plane while permitting movement of the medical instrument within that plane from a first orientation parallel to an axis of the imaging probe to a second orientation perpendicular to the axis of the imaging probe.

2. The apparatus of claim 1, further comprising a probe collar that fixably attaches to the imaging probe, said probe collar being hingeably coupled to said first link member to achieve said hingeable coupling of said first link member to the imaging probe.

3. The apparatus of claim 1, further comprising a handle that fixably attaches to the medical instrument, said handle being hingeably coupled to said second link member to achieve said hingeable coupling of said second link member to the medical instrument.

4. The apparatus of claim 1, wherein the number of intermediate link members is two.

5. The apparatus of claim 4, said first link member, said second link member, and said two intermediate link members being configured and dimensioned such that movement of the medical instrument within the scanning field plane selectively includes a third orientation 135 degrees from the axis of the imaging probe.

6. The apparatus of claim 5, said first link member, said second link member, and said two intermediate link members being configured and dimensioned such that movement of the medical instrument within the scanning field plane selectively includes a fourth orientation 180 degrees from the axis of the imaging probe.

7. The apparatus of claim 1, wherein there are at least four of said intermediate link members serially and hingeably coupled between said first and second link members.

8. The apparatus of claim 1, said intermediate link members being hingeably coupled between said first and second link members such that movement between any two adjacent link members is restricted around a hinge axis therebetween substantially perpendicular to the scanning field plane.

9. The apparatus of claim 8, wherein each of said link members comprises a rigid plastic material and is hingeably coupled to adjacent link members by a pin-in-slot hinge.

10. The apparatus of claim 8, wherein each of said link members comprises a rigid plastic material, and wherein adjacent link members are hingeably coupled using living hinges.

11. The apparatus of claim 10, wherein said link members are formed from a common sheet of low-cost plastic material into which grooves are cut to form said living hinges.

12. The apparatus of claim 1, further comprising a plurality of angle detectors, one for each of said hingeable couplings, for detecting current angles (i) between said imaging probe and said first link member, (ii) between adjacent first, intermediate, and second link members, and (iii) between said second link member and said medical instrument, respectively, and for communicating the current angles to an external computing device, the external computing device computing a current position of the medical instrument with respect to the imaging probe based on said current angles.

13. The apparatus of claim 12, wherein each angle detector between adjacent link members detects the current angle therebetween based on an inductive coupling effect that varies with the current angle.

14. The apparatus of claim 12, wherein each angle detector between adjacent link members comprises a potentiometer.

15. The apparatus of claim 14, wherein said potentiometer is affixed to its associated link members such that it also serves as said hingeable coupling therebetween.

16. The apparatus of claim 15, said potentiometer yielding a resistance reading according to an angle between first and second mechanical portions thereof, wherein said first mechanical portion is affixed to one of said associated link members and said second mechanical portion is affixed to the other.

17. The apparatus of claim 12, wherein said current angles between link members are communicated to the external computing device over an electric ribbon cable.

18. The apparatus of claim 12, wherein said current angles between link members are communicated to the external computing device using transmitters selected from the group consisting of: optical transmitters, infrared transmitters, radio transmitters, electromagnetic signal transmitters, and acoustic transmitters.

19. The apparatus of claim 12, the imaging probe being associated with a user display of an imaged portion of a subject patient, further comprising a computer program product associated with said external computing device, comprising:

computer code for receiving said current angles;

computer code for computing a current position of the medical instrument relative to the imaging probe using said current angles; and computer code for displaying a representation of the medical instrument on the user display for locations of overlap between the imaged portion and the medical instrument.

20. The apparatus of claim 19, further comprising computer code for predictively projecting the medical instrument onto the imaged portion based on the current position and orientation of the medical instrument relative to the imaging probe.

21. A biopsy guide for use in controlling the position of a biopsy needle relative to an ultrasound probe during an ultrasound-assisted biopsy procedure, the ultrasound probe scanning a patient along an imaged plane, comprising:

a first connector for fixable attachment to the ultrasound probe;

a second connector for fixable attachment to a handle of the biopsy needle; and a link assembly comprising at least three substantially rigid members hingeably connected to each other, said link assembly being hingeably connected to said first connector at one end and hingeably connected to said second connector at another end such that movement of the biopsy needle is substantially restricted to the imaged plane.

22. The biopsy guide of claim 21, wherein said link assembly comprises at least four substantially rigid members.

23. The biopsy guide of claim 21, wherein said link assembly comprises at least five substantially rigid members.

24. The biopsy guide of claim 21, said link assembly being configured and dimensioned such that the biopsy needle selectively moves within the imaged plane from a first orientation parallel to an axis of the ultrasound probe to a second orientation perpendicular to the axis of the imaging probe.

25. The biopsy guide of claim 24, said link assembly comprising at least five substantially rigid members configured and dimensioned such that the biopsy needle selectively enters a patient up to 10 cm away from the ultrasound probe at any angle between said first and second orientations in the imaged plane.

26. The biopsy guide of claim 24, said link assembly being configured and dimensioned such that the biopsy needle selectively moves within the imaged plane up to a third orientation 180 degrees from the axis of the imaging probe.

27. The biopsy guide of claim 21, wherein each link assembly member comprises a rigid plastic material and is hingeably coupled to adjacent link assembly members by a pin-in-slot hinge.

28. The biopsy guide of claim 21, wherein each link assembly member comprises a rigid plastic material, and wherein adjacent link assembly members are hingeably coupled using living hinges.

29. The biopsy guide of claim 28, wherein said link assembly members are formed from a common sheet of low-cost plastic material into which grooves are cut to form said living hinges, whereby said biopsy guide is low-cost and disposable.

30. The biopsy guide of claim 21, further comprising a plurality of angle detectors, one for each of said hingeable couplings, for detecting current angles (i) between said first connector and a first link assembly member, (ii) between adjacent link assembly members, and (iii) between a final link assembly member and said second connector, respectively, and for communicating the current angles to the ultrasound system associated with the ultrasound probe, the ultrasound system computing a current position of the biopsy needle with respect to the ultrasound probe based on said current angles.

31. The biopsy guide of claim 30, wherein each angle detector between adjacent link assembly members detects the current angle therebetween based on an inductive coupling effect that varies with the current angle.

32. The biopsy guide of claim 30, wherein each angle detector between adjacent link assembly members comprises a potentiometer.

33. The biopsy guide of claim 32, wherein said potentiometer is affixed to its associated link assembly members such that it also serves as said hingeable coupling therebetween.

34. The biopsy guide of claim 32, wherein said current angles between link members are communicated to the ultrasound system by one or more of the following methods: electrical transmission over ribbon cables; optical transmission, infrared transmission, radio transmission, electromagnetic signal transmission, and acoustic transmission.

35. The biopsy guide of claim 30, the ultrasound system displaying the imaged plane on a user display according to the current plane being scanned by the ultrasound probe, further comprising a computer program product associated therewith, comprising:
  computer code for receiving said current angles;
  computer code for computing a current position of the biopsy needle relative to the ultrasound probe using said current angles; and
  computer code for displaying a representation of the biopsy needle on the user display for locations of overlap between the imaged plane and the biopsy needle.

36. The biopsy guide of claim 35, further comprising computer code for predictively projecting the biopsy needle onto the user display based on the current position and orientation of the biopsy needle relative to the ultrasound probe.

37. An apparatus for use in an ultrasound-guided biopsy procedure in which a biopsy needle is inserted into a patient while an ultrasound probe scans the patient along an imaged plane, comprising:
  a link assembly comprising a plurality of substantially rigid link members, said link assembly being configured for hingeable attachment to the ultrasound probe at one end and for hingeable attachment to the biopsy needle at the other end such that movement of the biopsy needle is restricted to the imaged plane; and
  a plurality of position encoders respectively positioned at each interface between adjacent ones of said link members, between a first of said link members and the ultrasound probe, and between a last of said link members and the biopsy needle for detecting and providing relative position information such that a current position of the biopsy needle relative to the ultrasound probe can be computed.

38. The apparatus of claim 37, said position encoders providing said relative position information to an ultrasound system associated with said ultrasound probe.

39. The apparatus of claim 38, the ultrasound system having a user display that displays the imaged plane of the patient, further comprising a computer program product for use by the ultrasound system, the computer program product comprising:
  computer code for receiving said relative position information;
  computer code for computing said current position of the biopsy needle relative to the ultrasound probe using said relative position information; and
  computer code for displaying a representation of the biopsy needle on the user display for locations of overlap between the imaged plane and the biopsy needle.

40. The apparatus of claim 39, further comprising computer code for predictively projecting the biopsy needle onto the user display based on the current position and orientation of the biopsy needle relative to the ultrasound probe.

41. The apparatus of claim 37, said link members being hingeably attached to each other, said position encoders between said link members being angle detectors.

42. The apparatus of claim 41, said link assembly comprising at least four link members, said link assembly being configured and dimensioned such that the biopsy needle selectively moves within the imaged plane from a first orientation parallel to an axis of the ultrasound probe to a second orientation perpendicular to the axis of the imaging probe.

43. The apparatus of claim 42, said link assembly comprising at least five link members configured and dimensioned such that the biopsy needle selectively enters a patient up to 10 cm away from the ultrasound probe at any angle between said first and second orientations within the imaged plane.

44. The apparatus of claim 42, said link assembly being configured and dimensioned such that the biopsy needle selectively moves within the imaged plane up to a third orientation 180 degrees from the axis of the imaging probe.

45. The apparatus of claim 42, wherein each link member comprises a rigid plastic material and is hingeably coupled to adjacent link members by a pin-in-slot hinge.

46. The apparatus of claim 42, wherein each link member comprises a rigid plastic material, and wherein adjacent link members are hingeably coupled using living hinges.

47. The apparatus of claim 46, wherein said link members are formed from a common sheet of low-cost plastic material into which grooves are cut to form said living hinges, whereby said biopsy guide is low-cost and disposable.

48. The apparatus of claim 1, wherein the number of intermediate link members is three.

* * * * *